US00PP20071P3

(12) United States Plant Patent

Warren et al.

(10) Patent No.: US PP20,071 P3

(45) Date of Patent: Jun. 9, 2009

(54) *CALLA* LILY PLANT NAMED 'HOT CHERRY BLZ'

(50) Latin Name: ***Zantedeschia* spp.**
Varietal Denomination: Hot Cherry BLZ

(75) Inventors: Andrew G. F. Warren, Tauranga (NZ); Jacobus P. Spaans, Tauranga (NZ)

(73) Assignee: Bloomz Ltd, Tauranga (NZ)

( * ) Notice: Subject to any disclaimer, the term of this patent is extended or adjusted under 35 U.S.C. 154(b) by 98 days.

(21) Appl. No.: 11/787,815

(22) Filed: Apr. 18, 2007

(65) Prior Publication Data

US 2008/0263734 P1 Oct. 23, 2008

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Annette H Para
*Assistant Examiner*—Georgia Helmer
(74) *Attorney, Agent, or Firm*—Jondle & Associates, P.C.

(57) ABSTRACT

A *calla* lily plant particularly distinguished by a purple-red spathe, low density maculation of the leaves that is visible from both sides and which produces 2 to 4 inflorescences per 3-cm tuber, is described.

2 Drawing Sheets

Genus and species: *Zantedeschia* spp.
Variety denomination: 'Hot Cherry BLZ'.

BACKGROUND OF THE NEW PLANT

The present invention comprises a new and distinct cultivar of *calla* lily, botanically known as *Zantedeschia* spp., and hereinafter referred to by the cultivar name 'Hot Cherry BLZ'. The new cultivar was asexually reproduced from micropropagation resulting from the cross of the female parent *calla* lily, an unnamed seedling of *Zantedeschia* spp. (unpatented) with a pink spathe and the male parent *calla* lily 'Majestic Red' (patent status unknown) with a red/burgundy spathe.

The new cultivar was created in Tauranga, New Zealand and has been asexually reproduced repeatedly by micropropagation in India over a two-year period. The present invention has been found to retain its distinctive characteristics through successive propagations.

Plant Breeder's Rights for this cultivar were applied for in New Zealand on Oct. 6, 2006.

SUMMARY OF THE INVENTION

The following are the most outstanding and distinguishing characteristics of this new cultivar when grown under normal horticultural practices in Tauranga, New Zealand.

1. A purple-red spathe;
2. Low density maculation of the leaves that is visible from both sides; and
3. Produces 2 to 4 inflorescences per 3-cm tuber.

DESCRIPTION OF THE PHOTOGRAPHS

This new *calla* lily plant is illustrated by the accompanying photographs which show the mature inflorescence and foliage of the plant. The colors shown are as true as can be reasonably obtained by conventional photographic procedures. The photographs are of a plant approximately 9 weeks-old, after planting.

DESCRIPTION OF THE NEW CULTIVAR

Figure 1:
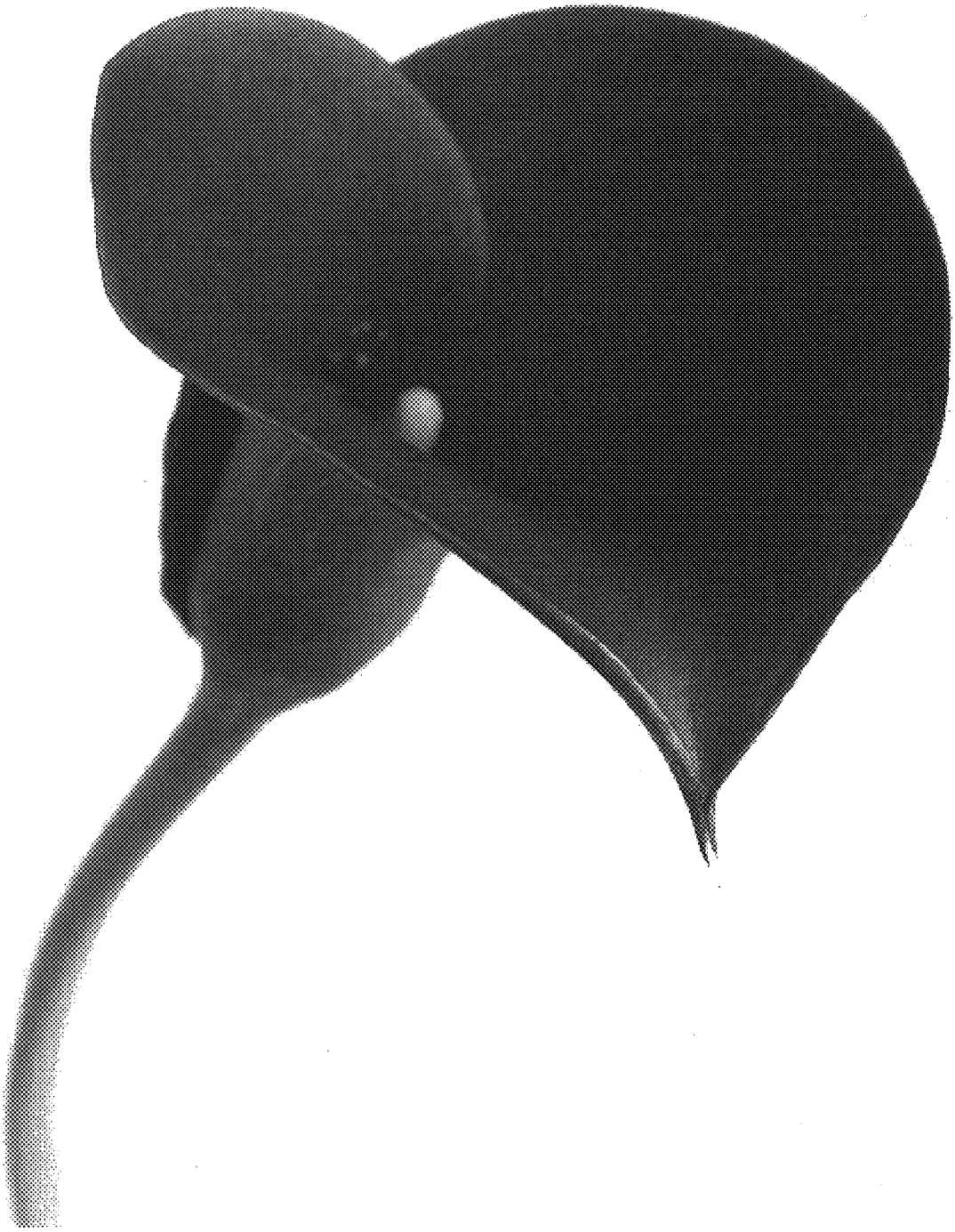
FIG. 1 shows a close-up of the mature inflorescence.
Figure 2:
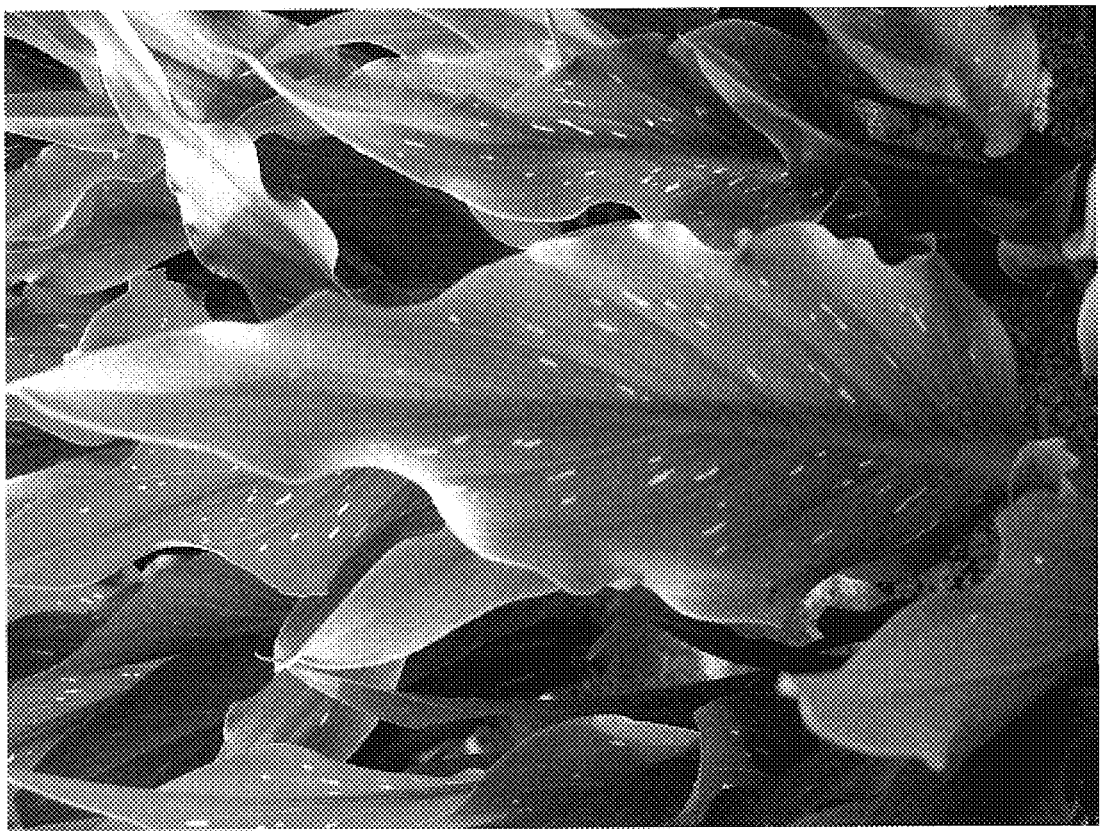
FIG. 2 shows a close of a mature leaf with maculation.

The following detailed description sets forth the distinctive characteristics of 'Hot Cherry BLZ'. The data that define these characteristics were collected from asexual reproductions carried out in Tauranga, New Zealand. The plant history was taken on two-year-old plants based on a 3-cm diameter tuber under New Zealand summer conditions. Color references are primarily to the R.H.S. Colour Chart of The Royal Horticultural Society of London (R.H.S.).

DETAILED BOTANICAL DESCRIPTION

Classification:
- *Family.*—Araceae.
- *Botanical name.*—*Zantedeschia* spp.
- *Common name.*—*Calla* lily.

Plant:
- *Form.*—Erect.
- *Height of the leaf canopy above the soil.*—45 cm to 55 cm.
- *Height of top of inflorescence above the soil.*—50 cm to 60 cm.
- *Diameter.*—25 cm to 35 cm.
- *Number of inflorescences per tuber size.*—Tuber diameter 3 cm: 2 to 4. Tuber diameter 4 cm: 3 to 6. Tuber diameter 5 cm: 6+.
- *Time to produce a finished flowering plant.*—6 to 10 weeks depending on the climate and environment.
- *Lastingness of inflorescence on the plant.*—2 to 3 weeks.

Tuber shoots:
- *Average number per plant.*—2 to 4.

*Character.*—Strong.

*Color.*—Upper surface: RHS 137C. Lower surface: RHS 146D. Base: RHS 155D.

Leaves:

*Size.*—Width: 8 cm to 11 cm. Length: 22 cm to 28 cm.

*Shape.*—Ovate.

*Color.*—Upper surface: RHS 137B. Lower surface: RHS 137D.

*Maculation* (*leaf spots*).—General: Maculation is only on the upper surface of the leaf but is visible from the lower surface. Density: Low density. Color: RHS 155C (white).

*Apex.*—Acute to apiculate.

*Base.*—Attenuate to shortly attenuate.

*Margin.*—Entire, moderately wavy.

*Margin color.*—RHS 145A (green).

*Venation pattern.*—Pinnate.

*Surface texture.*—Leathery.

*Petiole.*—Average number per tuber: 8 to 12. Length: 15 cm to 25 cm. Diameter: 0.6 cm to 1.2 cm. Color: Upper portion: RHS 137C. Base: RHS 146D. Texture: Smooth. Character: Strong. Sheath: Width: 0.6 cm to 0.8 cm. Length: 2 cm to 5 cm. Color: RHS 137C (green).

Roots:

*Color.*—RHS 155D (white).

*Branching.*—Not branched, attached to the top of the tuber at apices.

Inflorescence:

*Spathe* (*flower body*).—Size: Length: 7 cm to 9 cm. Height: 8 cm to 10 cm. Width: 5 cm to 6 cm. Color: Upper part: RHS 60A. Lower part: RHS 60C. Veins: RHS 59A. Shape: Fluted. Texture: Smooth. Apex: Caudate. Base: Attenuate. Margin: Entire.

*Fragrance.*—Absent.

*Spadix* (*reproductive organs*).—Size: Length: 2.5 cm to 3.5 cm. Diameter: 0.6 cm to 0.8 cm. Color: Base: RHS 60B. Upper part: RHS 15B. Position relative to spathe: Upright. Shape: Elongated. Apex: Rounded.

*Peduncle* (*flower stem*).—Length: 35 cm to 55 cm. Diameter: 0.7 cm to 1.1 cm. Color: Base: RHS 155A. Upper part: RHS 60B. Texture: Smooth. Strength: Strong.

Reproductive organs:

*Location of female organs.*—Basal position of the spadix.

*Location of male organs.*—Upper position of the spadix.

*Perianth* (*the floral envelope, calyx and corolla*).—Conspicuous.

*Stamens.*—Not visible before pollen release.

*Pollen color.*—RHS 155D (white).

*Pistil.*—Number: 25 to 35 per spadix. Color: RHS 17B.

Fruit:

*General.*—Whole fruit is 2.5 cm to 3.5 cm wide and 4.0 cm to 5.0 cm long; individual berries are round and 0.5 cm to 0.7 cm in circumference.

*Number.*—8 to 15 berries per plant.

*Color.*—RHS 144A.

Disease and insect resistance:

*Disease resistance.*—No susceptibility noted to date.

*Pest resistance.*—No susceptibility noted to date.

COMPARISON WITH PARENTAL AND COMMERCIAL CULTIVARS

When the instant plant is compared to the female parent, an unnamed seedling of *Zantedeschia* spp. (unpatented), 'Hot Cherry BLZ' has darker pink spathes and larger spathes than the female parent.

When 'Hot Cherry BLZ' is compared to the male parent, 'Majestic Red' (patent status unknown), 'Hot Cherry BLZ' has a brighter (lighter) spathe color and more inflorescences than the male parent.

'Hot Cherry BLZ' differs from the commercial cultivar 'Hot Lips' (U.S. Plant Pat. No. 15,260) in that 'Hot Cherry BLZ' has a higher spathe count, more consistently shaped spathes and the spathe color is more purple-red, while the spathe color of 'Hot Lips' is more pink.

I claim:

1. A new and distinct cultivar of *calla* lily plant as shown and described herein.

* * * * *